United States Patent
Yaqub et al.

(10) Patent No.: US 9,034,350 B2
(45) Date of Patent: May 19, 2015

(54) CLEANSING COMPOSITION

(75) Inventors: Najem Yaqub, Oldham (GB); Roxanne Bullen, Didsbury (GB); Helen Patricia Atkinson, Gatley (GB)

(73) Assignee: PZ Cussons (International) Limited (GB)

( * ) Notice: Subject to any disclaimer, the term of this patent is extended or adjusted under 35 U.S.C. 154(b) by 373 days.

(21) Appl. No.: 10/824,202

(22) Filed: Apr. 14, 2004

(65) Prior Publication Data

US 2004/0258650 A1    Dec. 23, 2004

(30) Foreign Application Priority Data

Apr. 14, 2003    (GB) .................................. 0308584.2

(51) Int. Cl.
| | |
|---|---|
| *C11D 3/00* | (2006.01) |
| *A61K 8/04* | (2006.01) |
| *A61K 8/39* | (2006.01) |
| *A61K 8/44* | (2006.01) |
| *A61K 8/46* | (2006.01) |
| *A61Q 19/10* | (2006.01) |
| *C11D 1/83* | (2006.01) |
| *C11D 1/29* | (2006.01) |
| *C11D 1/66* | (2006.01) |
| *C11D 1/72* | (2006.01) |
| *C11D 1/75* | (2006.01) |

(52) U.S. Cl.
CPC .............. *C11D 3/0094* (2013.01); *A61K 8/046* (2013.01); *A61K 8/39* (2013.01); *A61K 8/442* (2013.01); *A61K 8/463* (2013.01); *A61K 2800/596* (2013.01); *A61Q 19/10* (2013.01); *C11D 1/29* (2013.01); *C11D 1/667* (2013.01); *C11D 1/72* (2013.01); *C11D 1/75* (2013.01); *C11D 1/83* (2013.01)

(58) Field of Classification Search
USPC ........................................................ 424/401
See application file for complete search history.

(56) References Cited

U.S. PATENT DOCUMENTS

| | | | | |
|---|---|---|---|---|
| 4,772,427 | A * | 9/1988 | Dawson et al. ............... | 510/158 |
| 6,033,647 | A | 3/2000 | Touzan et al. | |
| 6,440,923 | B1 * | 8/2002 | Lyle et al. ..................... | 510/406 |
| 2002/0122772 | A1 * | 9/2002 | Lukenbach et al. ........... | 424/44 |

FOREIGN PATENT DOCUMENTS

| | | |
|---|---|---|
| EP | 0 990 436 | 4/2000 |
| EP | 1 295 588 | 3/2003 |
| GB | 2 213 160 | 8/1989 |
| WO | WO 94/02109 | 2/1994 |
| WO | WO 96/09032 | 3/1996 |
| WO | WO 97/03646 | 2/1997 |
| WO | WO 00/39273 | 7/2000 |
| WO | WO 02/05758 | 1/2002 |
| WO | WO 03/084501 | 10/2003 |

* cited by examiner

*Primary Examiner* — Mina Haghighatian
*Assistant Examiner* — Luke Karpinski
(74) *Attorney, Agent, or Firm* — Salter & Michaelson

(57) ABSTRACT

A post-foaming cleansing composition comprises at least one anionic surfactant, at least one non-ionic gelling agent and at least one post-foaming agent. The ratio of anionic surfactant: non-ionic gelling agent is 4:1 or greater such that during manufacture a gel structure is formed. The gel structure remains substantially unchanged for at least 4 minutes after the addition of the said post-foaming agent to the remainder of the composition.

30 Claims, No Drawings

CLEANSING COMPOSITION

TECHNICAL FIELD

The present invention relates to a cleansing composition and more particularly a personal cleansing composition intended for use in a shower.

BACKGROUND

Personal cleansing compositions have been developed for use in showers, such as shower gels. However, large numbers of people prefer to use a conventional bar of soap rather than a shower gel. It is believed that one factor responsible for resistance to the use of shower gels is connected to lather generation. In order to produce lather from a shower gel the user must apply shear to the gel. In some cases much of this effort is wasted as the lather washes away before it can be applied to the body.

In order to deal with the problem it is known to provide a shower gel which creates lather as soon as possible after the gel is dispensed from the package.

WO 96/09032A discloses a soap-free post-foaming gel composition which is particularly intended for shaving using a razor. The composition utilises a volatile hydrocarbon such as isopentane to provide a gel structure. Although this composition is satisfactory for its intended purpose it does not perform well for personal washing mainly because it gives an uncomfortable 'stripped' feeling to the skin.

WO 97/03646 discloses a post-foaming gel composition for use in an aerosol container wherein the composition comprises a base material having a viscosity of at least 9500 cps to which is added a foam-forming propellant gas. Whilst this composition has good personal washing properties its viscous nature makes it particularly difficult to process and package and thus there is a high degree of wastage during manufacture.

Attempts have been made to address this problem. For example, WO00/39273 discloses a post-foaming composition of low viscosity which gels upon addition of the post-foaming agent. However, this sudden, instantaneous gelling can make the composition difficult to fill into suitable packaging and may lead to stoppages and breakdowns in the pipe-work of the production plant machinery resulting in plant downtime and inefficient production. This formulation must be filled into required packaging immediately on addition of the post-foaming agent.

Similarly, GB 2,213,160 teaches of a post foaming gel product containing an anionic surfactant and a non-ionic, ethoxylated fatty alcohol or ester. The product gels on addition of post-foaming agent and forms a viscous gel prior to filling into a suitable container. This again presents difficulties in terms of manufacturing due to the high viscosity of the gel formed.

WO 02/05758 discloses a self foaming composition wherein the composition is in the form of a liquid crystalline structure. This results in a soft gel of lower viscosity. Whilst the soft gel is easier to spread onto the skin it has a number of disadvantages compared to a more structured viscous gel. A more viscous gel will release the post-foaming agent more slowly on agitation and lather is developed in a more controlled manner. Thus it appears that the user is responsible for creating the foam as with conventional cleaning materials and the composition is perceived as providing the behaviour expected for a good cleaning operation. The lather generated from a more viscous gel is creamier than that generated from a soft gel. An additional benefit of a viscous gel is that the product can be spread further over the body without being washed away as with conventional products. Thus, it appears to the user that the product is more economical.

Many of the post-foaming compositions currently available have an opaque or cloudy appearance. This provides poor visual differentiation between the initial gel which is dispensed and the lather generated when the gel is spread onto the skin. As such, these compositions lack visual appeal.

It is desirable therefore to provide a post-foaming cleansing composition which is sufficiently mobile to facilitate easy processing and packaging, but which has a stable, clear, viscous gel structure when dispensed from its packaging and which enables slow release of a post-foaming agent and provides a creamy lather. It is also desirable to provide a post-foaming cleansing composition which gives acceptable post washing skin feel i.e. does not the leave the skin feeling dry and tight.

THE INVENTION

According to the present invention there is provided a post-foaming cleansing composition comprising at least one anionic surfactant, at least one non-ionic gelling agent and at least one post-foaming agent, characterised in that the ratio of anionic surfactant:non-ionic gelling agent is 4:1 or greater, such that during manufacture the gel rigidity of the composition remains substantially unchanged for at least 4 minutes after addition of the said post-foaming agent to the remainder of the composition.

Advantageously, the gel structure of the composition of the present invention does not begin to form for a sufficient period of time during the processing and packaging of the composition such that it can be easily pumped and filled into the packaging. Furthermore, there is no gel formation within plant pipe-work and so stoppages and breakages are minimised.

A further advantage of the present invention is that due to the delayed gelling elevated pressure is not required to pump the composition through the pipe-work. This not only reduces the manufacturing costs of the end product, but it also increases the filling rates meaning more units of composition of the present invention can be produced in the same time period relative to previously available compositions.

A still further advantage of the present invention is that, due to the presence of the non-ionic gelling agent, once the composition has been filled into the packaging and allowed to stand the viscosity of the composition and therefore its gel rigidity increases. This gives rise to a composition which provides a non-mobile, shear thinning, viscous gel upon dispensing from the packaging. Thus, neither the appearance of the gel on first dispensing from the packaging nor the quality of the lather produced upon agitating the gel by the user is compromised for the sake of ease of manufacturing.

A further advantage of the present invention is that the gels produced are clear. This clarity of the gel provides an indication to the consumer of the high product quality and further differentiates visually the product. A clear gel also makes the inclusion of pigments much easier. Furthermore, the clarity of the gel of the present invention remains substantially unchanged throughout the lifetime of the product.

Due to the volatility of the post-foaming agent, it is not possible to accurately measure the viscosity of the composition following the addition of the post-foaming agent i.e. the gelled composition. Therefore, the gel rigidity of the composition is used as a measure of the extent to which a composition has gelled.

The gel rigidity test is conducted at ambient temperature of 20 to 25° C. where both the can and its contents are at this temperature. The can is held approximately 2 inches above a white sheet of paper and actuated for 2 seconds to dispense the gel. The characteristics of the gel are observed and scored for Rigidity (R) using the following arbitrary rigidity rating scale:—

R=1 Rigid gel with no visible mobility

Gel retains its shape until the post-foaming agent starts to be released and the gel starts to turn into a foam R=2 Firm gel with some visible mobility Gel starts to form into an amorphous mound before the post-foaming agent starts to be released and the gel starts to turn into a foam R=3 Firm gel with some visible mobility which collapses slowly Gel forms an amorphous mound on dispensing which slowly spreads R=4 Thin gel/mobile liquid Gel has viscous appearance but spreads rapidly after dispensing R=5 Thin liquid Gel has a non-viscous appearance and is runny after dispensing By substantially unchanged it is meant that the score for gel rigidity of the composition does not change by more than 1 unit on the rigidity rating scale.

A particularly important feature of the composition of the present invention is the non-ionic gelling agent. It is thought that it is the non-ionic gelling agent with the surfactants of the present invention which is responsible for the delayed gelling of the composition during manufacture.

Upon addition of the post-foaming agent the composition has a gel rigidity rating score of 3 units or more and more preferably 4 units or more. At this time the composition can be described as a thin mobile gel or liquid. Once the composition begins to form a gel structure it does so such that the composition has a final gel rigidity rating score of R=1 or 2 or more preferably R=1.

Preferably the gel rigidity of the composition remains substantially unchanged for at least 10 minutes after addition of the post-foaming agent to the remainder of the composition and most preferably for at least 30 minutes after addition of the post-foaming agent to the remainder of the composition.

It is difficult to measure clarity of a post foaming gel when first dispense because it will start to become cloudy on release of the post foaming agent from the gel structure. For this reason the clarity of the gel is measured using a Gel Clarity Rating scale.

The gel clarity test is conducted at ambient temperature of 20° C. to 25° C., where both the can and its contents are at this temperature. The can is held approximately 2 inches above a white sheet of feint ruled paper and actuated to dispense a 3 inch line of gel.

The characteristics of the gel are observed and scored for Clarity using the following arbitrary clarity rating scale:—

| | |
|---|---|
| C = 1 Perfect Clarity | Clear gel, Lines are easily defined |
| C = 2 Standard Clarity | Clear gel, lines are visible |
| C = 3 Minor Clouding | Hazy Gel - Lines are not clearly defined |
| C = 4 Major Clouding | Hazy Gel - lines are not clearly visible |
| C = 5 Critical Clouding | Cloudy gel - lines are obscured |

It is desirable therefore that the formulation when dispensed forms a gel with a clarity rating score of C=1 or 2, more preferably C=1.

By substantially unchanged it is meant that the score for gel clarity of the composition does not change by more than 1 unit on the clarity rating scale.

Suitable non-ionic gelling agents which can be used alone or in combination include alkoxylated alcohols, glyceryl esters, glycol esters, alkoxylated carboxylic acids, alkanolamides and their derivatives. Preferred non-ionic gelling agents include alkoxylated alcohols such as laureth-2, laureth-4, C12/13 pareth-3, ceteareth-4 or oleth-3 or glycol esters such as coconut fatty acid monoglyceride polyglycol ether or modified palm oil polyglycol ether.

The particularly preferred non-ionic gelling agents are laureth-4 and/or PEG 7 glyceryl cocoate.

The non-ionic gelling agent shall preferably constitute from 0.01% to 8.0% by weight, more preferably from 0.01% to 4.0% by weight and most preferably from 0.5% to 2.5% by weight of the total composition.

Suitable anionic surfactants include alkali metal alkyl ether sulfates, sulfosuccinates, isethionates and acyl glutamates. In addition to at least one anionic surfactant the composition of the present invention preferably further comprises at least one amphoteric surfactant such as betaines.

A particularly preferred anionic surfactant is sodium lauryl ether sulphate and particularly preferred amphoteric surfactant is cocamidopropyl betaine.

The total surfactant shall preferably constitute from 0.01% to 30.0% by weight of the total composition and more preferably from 15% to 28% by weight of the total composition and most preferably from 18% to 25% by weight of the total composition. Where the surfactant component comprises more than one surfactant the anionic surfactant shall preferably be the major surfactant and as such constitute at least 50% by weight of the total surfactant.

In addition to the at least one anionic surfactant the composition of the present invention may comprise further surfactants, which may be used alone or in combination, and include any of the following:—anionic, cationic, non-ionic, amphoteric (zwitter-ionic) surfactants.

Specific surfactants which may be used alone or in combination include any of the following:—alkyl polyglucosides, ethoxylated and non-ethoxylated metal alkyl sulfates, sultaines, taurates, betaines, sarcosinates, sulfosuccinates, sulfonates, carboxylates, glycinates, amphoacetates, amphodiacetates, isethionates, quaternary ammonium compounds, polysorbates, sugar esters, alkyl phosphates, propionates, amino acid surfactants, glucosides, alkanolamides and betaines.

The post-foaming agent used in the composition of the present invention is chosen largely out of consideration for the particular type of composition that is being formulated.

The preferred post-foaming agent comprises at least one saturated aliphatic hydrocarbon having from 4 to 6 carbons such as n-butane, iso-butane, n-pentane, iso-pentane, iso-hexane and mixtures thereof.

The post-foaming agent preferably constitutes from 0.01% to 14% by weight and most preferably from 7% to 11% by weight of the total composition.

Additional ingredients may be added to the composition of the present invention including any of the following:—fragrances, essential oils, plant extracts, antimicrobial agents, colouring agents, skin conditioning agents, humectants preservatives, pearlisers, opacifiers, pH modifiers, shimmering agents, exfoliants, silicone oils, lipids, vitamins, sunscreen agents, skin lightening agents, and mixtures thereof.

Suitable additional ingredients include those which do not affect the gel rigidity of the composition of the present invention thereby avoiding a low viscosity product.

Typically, at a least some of the ingredients of cleansing compositions such as those described herein, are solids and/or powders. This can give rise to mixing problems as it is more difficult to achieve a homogeneous mixture when some of the components are solids. Furthermore, it may be necessary to heat some of the components thus providing a hot batch mixing process. This introduces extra processing steps and manufacturing costs.

Thus, the components of the present invention are preferably liquid in order that manufacturing is facilitated.

The present invention is packaged in a container that is suitable for dispensing a post-foaming gel for example a bag on valve system, a bag in can system or an elasticated bladder container. These types of containers are well known to those skilled in the art.

The composition of the present invention may be provided as a concentrate which can be diluted prior to use.

According to the second aspect of the present invention there is provided a method for the manufacture of a post-foaming cleansing composition comprising the steps of:—adding at least one non-ionic gelling agent to a mixture comprising at least one anionic surfactant such that the ratio of anionic surfactant:non-ionic gelling agent is 4:1 or greater, combining the ensuing mixture with at least one post-foaming agent and filling the mixture into a package prior to a gel structure being formed and wherein the gel rigidity of the composition remains substantially unchanged for at least 4 minutes after addition of the said post-foaming agent to the said mixture.

In order that the present invention is more readily understood the composition of the present invention will now be described further by way of example only and with reference to the following examples. Examples 1a and 1d do not form part of the present invention.

Base Formulation for Examples 1a to 1d

| Component | Function | Quantity (% w/w) |
|---|---|---|
| Water | Solvent | 68.80-75.00 |
| Disodium EDTA | Chelating Agent | 0.05-0.30 |
| Citric Acid | pH Adjuster | 0.05-0.30 |
| Methyldibromo Glutaronitrile and Phenoxyethanol | Preservative | 0.05-0.10 |
| Sodium Laureth Sulfate | Primary Surfactant | 17.50-22.00 |
| Cocamidopropyl Betaine | Foam Booster | 0.5-3.00 |
| PEG-7 Glyceryl Cocoate | Skin conditioning agent/non-ionic gelling agent | 0.50-1.50 |
| Glycerin | Skin conditioning agent | 0.10-2.00 |
| Colour | Colourant | 0.0005-0.0010 |
| Parfum | Masking Agent | 0.70 |
| Laureth-4 | Gelling Agent | As table below |

Examples 1a to 1d

| Formulation | % Laureth 4 | Viscosity @ 20° C. | Appearance of Gel Concentrate | Time to reach R = 1 | Finished Product Gel Appearance/Rigidity |
|---|---|---|---|---|---|
| 1a | 0 | 226 cP (Spindle RV 4 Speed 10) | Clear Thin Liquid | Achieves R = ⅔ after 60 minutes Does not achieve R = 1 | Soft Cloudy Gel R = ⅔ C = 4 |
| 1β | 1.00 | 750 cP (Spindle RV 4 Speed 10) | Clear Thin Liquid | 40 minutes | Clear Rigid Gel R = 1 C = 1 |
| 1c | 1.25 | 1020 cP (Spindle RV 4 Speed 10) | Clear Thin Liquid | 20 minutes | Clear Rigid Gel R = 1 C = 1 |
| 1d | 8.25 | 424,000 cP (Spindle RV 5 Speed 0.5) | Cloudy Viscous Gel | Instantly achieves R = ⅔ Does not achieve R = 1 | Soft Cloudy Gel R = ⅔ C = 4 |

Viscosity is measured on a Brookfield Sinchro-lectric Viscometer

"Time to reach R = 1 (mins)" refers to the time taken, in minutes, for the composition to form a rigid gel with no visible rigidity following addition of the post foaming agent.

The gel rigidity was determined using the test described herein before.

The examples referred to above were prepared in the following manner:—
1. De-ionised water was placed in a suitable vessel.
2. The chelating agent was dissolved in the water
3. The primary surfactant and foam booster were slowly added to the solution with stirring. Stirring was continued until all materials were completely dissolved.
4. The colorant was added to the mixture until completely dispersed.
5. The preservative and glycerin were added to the mixture and stirred until completely dissolved
6. The skin conditioning agent and Fragrance were premixed until homogeneous
7. The premix was then added to the mixture and stirred until completely dissolved.
8. The non-ionic gelling agent was added to the mixture and stirred until fully dissolved.
9. The pH was adjusted to pH 5.0-6.0 with Citric acid.
10. The post foaming agent was stirred into the mixture.
11. The mixture was immediately filled into a suitable aerosol can for a post foaming gel composition.
12. The gel was dispensed from the can at regular intervals following filling and graded for gel rigidity. The time taken to achieve a maximum gel rigidity was recorded.

It is of course to be understood that the invention is not intended to be restricted to the details of the above embodiments which are described by way of example only.

The invention claimed is:

1. A post-foaming cleansing composition comprising at least one anionic surfactant together with at least one amphoteric surfactant, said amphoteric surfactant constituting from 0.5% to 3.0% by weight of the total composition, at least one non-ionic gelling agent and at least one post-foaming agent, characterised in that the ratio of anionic surfactant:non-ionic gelling agent is 4:1 or greater such that during manufacture the rigidity of the composition always remains substantially unchanged for at least 4 minutes after addition of the said post-foaming agent to the remainder of the composition, wherein the non-ionic gelling agent is selected from alkoxylated alcohols laureth-2, laureth-4, C12/13 pareth-3, ceteareth-4, or oleth-3 alone or in combination, and wherein the at least one non-ionic gelling agent constitutes from 0.5% to 2.5% by weight of the total composition, wherein the composition is filled into a package from which the subsequently formed gel is dispensed, wherein the composition is filled into the package prior to the gel structure being formed, wherein the foregoing steps are performed absent any applied elevated pressure; and wherein the package is selected from the group comprising a bag on valve container, a bag in can container and an elasticated bladder container, wherein the rigidity of the composition remains substantially unchanged for the at least 4 minutes and in accordance with a gel rigidity rating scale of:

R=1 Rigid gel with no visible mobility,
Gel retains its shape until the post-foaming agent starts to be released and the gel starts to turn into a foam;
R=2 Firm gel with some visible mobility
Gel starts to form into an amorphous mound before the post-foaming agent starts to be released and the gel starts to turn into a foam;
R=3 Firm gel with some visible mobility which collapses slowly
Gel forms an amorphous mound on dispensing which slowly spreads;
R=4 Thin gel/mobile liquid
Gel has viscous appearance but spreads rapidly after dispensing;
R=5 Thin liquid
Gel has a non-viscous appearance and is runny after dispensing;
and wherein the rigidity of the composition remains substantially unchanged for the at least four minutes at a gel rigidity rating of at least R4 after the addition of said post-forming agent to the mixture, and then after said at least four minutes transitions to a rigidity rating of R1 or R2.

2. A post-foaming cleansing composition as claimed in claim 1, wherein the non-ionic gelling agent consists of laureth-4.

3. A post-foaming cleansing composition according to claim 1, wherein the composition is filled into an aerosol can prior to the gel structure being formed.

4. A post-foaming cleansing composition according to claim 1, wherein the total surfactant constitutes from about 0.01% to about 30.0% by weight of the total composition.

5. A post-foaming cleansing composition according to claim 1, wherein the post-foaming agent comprises at least one saturated aliphatic hydrocarbon having from 4 to 6 carbons.

6. A post-foaming cleansing composition according to claim 1, wherein the post-foaming agent constitutes from about 0.01% to about 14% by weight of the total composition.

7. A method for the manufacture of a cleansing composition comprising the steps of:—adding at least one non-ionic gelling agent to a mixture comprising at least one anionic surfactant, together with at least one amphoteric surfactant, said amphoteric surfactant constituting from 0.5% to 3.0% by weight of the total composition, such that the ratio of anionic surfactant: non-ionic gelling agent is 4:1 or greater, combining the ensuing mixture with at least one post-foaming agent and filling the mixture into a package, from which the subsequently formed gel is dispensed, prior to a gel structure being formed and, wherein the rigidity of the composition remains substantially unchanged for at least 4 minutes after addition of the said post-foaming agent to the said mixture, wherein the non-ionic gelling agent is selected from alkoxylated alcohols laureth-2, laureth-4, C12/13 pareth-3, ceteareth-4, or oleth-3 alone or in combination, wherein the at least one non-ionic gelling agent constitutes from about 0.5% to 2.5% by weight of the total composition, wherein the foregoing steps are performed absent any applied elevated pressure; and wherein the package is selected from the group comprising a bag on valve container, a bag in can container and an elasticated bladder container, wherein the rigidity of the composition remains substantially unchanged for the at least 4 minutes and in accordance with a gel rigidity rating scale of:

R=1 Rigid gel with no visible mobility,
Gel retains its shape until the post-foaming agent starts to be released and the gel starts to turn into a foam;
R=2 Firm gel with some visible mobility
Gel starts to form into an amorphous mound before the post-foaming agent starts to be released and the gel starts to turn into a foam;
R=3 Firm gel with some visible mobility which collapses slowly
Gel forms an amorphous mound on dispensing which slowly spreads;
R=4 Thin gel/mobile liquid
Gel has viscous appearance but spreads rapidly after dispensing;
R=5 Thin liquid
Gel has a non-viscous appearance and is runny after dispensing;
and wherein the rigidity of the composition remains substantially unchanged for the at least four minutes at a gel rigidity rating of at least R4 after the addition of said post-forming agent to the mixture, and then after said at least four minutes transitions to a rigidity rating of R1 or R2.

8. A post-foaming cleansing composition according to claim 2, wherein the total surfactant constitutes from about 0.01% to about 30.0% by weight of the total composition.

9. A post-foaming cleansing composition according to claim 2, wherein the post-foaming agent comprises at least one saturated aliphatic hydrocarbon having from 4 to 6 carbons.

10. A post-foaming cleansing composition according to claim 4, wherein the post-foaming agent comprises at least one saturated aliphatic hydrocarbon having from 4 to 6 carbons.

11. A post-foaming cleansing composition according to claim 2, wherein the post-foaming agent constitutes from about 0.01% to about 14% by weight of the total composition.

12. A post-foaming cleansing composition according to claim 4, wherein the post-foaming agent constitutes from about 0.01% to about 14% by weight of the total composition.

13. A post-foaming cleansing composition according to claim 5, wherein the post-foaming agent constitutes from about 0.01% to about 14% by weight of the total composition.

14. A post-foaming cleansing composition according to claim 1 wherein the anionic surfactant comprises sodium lauryl ether sulphate.

15. A post-foaming cleansing composition according to claim 1 wherein the anionic surfactant includes alkali metal alkyl ether sulfates, sulfosuccinates, isethionates and acyl glutamates.

16. A post-foaming cleansing composition according to claim 1 wherein the post-foaming agent includes n-butane, iso-butane, n-pentane, iso-pentane, iso-hexane and mixtures thereof.

17. A post-foaming cleansing composition according to claim 1 wherein the post-foaming agent includes iso-pentane.

18. A post-foaming cleansing composition according to claim 1 wherein the anionic surfactant comprises the major surfactant and thus constitutes more than 50 percent by weight of the total surfactant.

19. A post-foaming cleansing composition according to claim 1 wherein the amphoteric surfactant includes cocamidopropyl betaine.

20. A post-foaming cleansing composition according to claim 1 wherein the manufacturing is performed through plant pipe-work, the at least one post-foaming agent providing a delayed gelling, and due to the delayed gelling the elevated pressure is not required in order to pump the composition through the pipe-work.

21. A post-foaming cleansing composition according to claim 20 wherein the applied elevated pressure is at least 80 psi or more.

22. A method according to claim 7 wherein the foregoing steps are performed through plant pipe-work, the at least one post-foaming agent providing a delayed gelling, and due to the delayed gelling the elevated pressure is not required in order to pump the composition through the pipe-work.

23. A method according to claim 22 wherein the applied elevated pressure is at least 80 psi or more.

24. A method for enhancing the efficiency of the manufacture of a post-foaming cleansing composition in a plant having pipe-work, said method comprising the steps of:—providing a liquid mixture of at least one non-ionic gelling agent and at least one anionic surfactant, together with at least one amphoteric surfactant, said amphoteric surfactant constituting from 0.5% to 3.0% by weight of the total composition, such that the ratio of anionic surfactant: non-ionic gelling agent is 4:1 or greater, combining the ensuing mixture with at least one post-foaming agent but with a delayed gelling, filling the mixture into a package, from which the subsequently formed gel is dispensed, prior to a gel structure being formed and, wherein the rigidity of the composition remains substantially unchanged for at least 4 minutes after addition of the said post-foaming agent to the said mixture, wherein the gel structure is only formed at least 4 minutes after the addition of the post-foaming agent to the mixture, wherein the step of filling the mixture into a package prior to the formation of the gel structure includes filling the mixture into a final container from which the composition is later dispensed for direct personal use, wherein the non-ionic gelling agent is selected from alkoxylated alcohols laureth-2, laureth-4, C12/13 pareth-3, ceteareth-4, or oleth-3 alone or in combination, wherein the at least one non-ionic gelling agent constitutes from 0.5% to 2.5% by weight of the total composition, wherein the foregoing steps are performed absent any applied elevated pressure; and wherein the final container is selected from the group comprising a bag on valve container, a bag in can container and an elasticated bladder container, wherein the rigidity of the composition remains substantially unchanged for the at least 4 minutes and in accordance with a gel rigidity rating scale of:

R=1 Rigid gel with no visible mobility,

Gel retains its shape until the post-foaming agent starts to be released and the gel starts to turn into a foam;

R=2 Firm gel with some visible mobility

Gel starts to form into an amorphous mound before the post-foaming agent starts to be released and the gel starts to turn into a foam;

R=3 Firm gel with some visible mobility which collapses slowly

Gel forms an amorphous mound on dispensing which slowly spreads;

R=4 Thin gel/mobile liquid

Gel has viscous appearance but spreads rapidly after dispensing;

R=5 Thin liquid

Gel has a non-viscous appearance and is runny after dispensing;

and wherein the rigidity of the composition remains substantially unchanged for the at least four minutes at a gel rigidity rating of at least R4 after the addition of said post-forming agent to the mixture, and then after said at least four minutes transitions to a rigidity rating of R1 or R2.

25. A post-foaming cleansing composition according to claim 1 wherein the amphoteric surfactant constitutes from 0.5% to 1.5% by weight of the total composition.

26. A method for enhancing the efficiency of the manufacture of a post-foaming cleansing composition in a plant having pipe-work, said method comprising the steps of:—providing a liquid mixture of at least one non-ionic gelling agent and at least one anionic surfactant, together with at least one amphoteric surfactant, said amphoteric surfactant constituting from 0.5% to 3.0% by weight of the total composition, such that the ratio of anionic surfactant: non-ionic gelling agent is 4:1 or greater, combining the ensuing mixture with at least one post-foaming agent but with a delayed gelling, filling the mixture into a package, from which the subsequently formed gel is dispensed, prior to a gel structure being formed and, wherein the rigidity of the composition remains substantially unchanged for at least 4 minutes after addition of the said post-foaming agent to the said mixture, wherein the gel structure is only formed at least 4 minutes after the addition of the post-foaming agent to the mixture, wherein the step of filling the mixture into a package prior to the formation of the gel structure includes filling the mixture into a final container from which the composition is later dispensed for direct personal use, wherein the non-ionic gelling agent is selected from alkoxylated alcohols laureth-2, laureth-4, C12/13 pareth-3, ceteareth-4, or oleth-3 alone or in combination, wherein the at least one non-ionic gelling agent constitutes from about 0.5% to 2.5% by weight of the total composition, wherein the foregoing steps are performed absent any applied elevated pressure; and wherein the final container is selected from the group comprising a bag on valve container, a bag in can container and an elasticated bladder container wherein the rigidity of the composition remains substantially unchanged for the at least 4 minutes and in accordance with a gel rigidity rating scale of:

R=1 Rigid gel with no visible mobility

Gel retains its shape until the post-foaming agent starts to be released and the gel starts to turn into a foam;

R=2 Firm gel with some visible mobility

Gel starts to form into an amorphous mound before the post-foaming agent starts to be released and the gel starts to turn into a foam;

R=3 Firm gel with some visible mobility which collapses slowly

Gel forms an amorphous mound on dispensing which slowly spreads;

R=4 Thin gel/mobile liquid

Gel has viscous appearance but spreads rapidly after dispensing;

R=5 Thin liquid

Gel has a non-viscous appearance and is runny after dispensing;

and wherein the rigidity of the composition remains substantially unchanged for the at least four minutes at a gel rigidity rating of at least R4 after the addition of said post-forming agent to the mixture, and then after said at least four minutes transitions to a rigidity rating of R1 or R2.

27. The method of claim 26 wherein by substantially unchanged it is meant that the score for gel rigidity rating of the composition does not change by more than 1 unit on the rigidity rating scale.

28. The method of claim 27 wherein the characteristics of the gel are observed and scored for clarity using the following clarity rating scale:

C=1 Perfect Clarity Clear gel, Lines are easily defined;

C=2 Standard Clarity Clear gel, lines are visible;

C=3 Minor Clouding Hazy Gel—Lines are not clearly defined;

C=4 Major Clouding Hazy Gel—lines are not clearly visible;

C=5 Critical Clouding Cloudy gel—lines are obscured and wherein the formulation, when dispensed, forms a gel with a clarity rating score of C=1 or C=2.

29. The method of claim 28 wherein by substantially unchanged it is meant that the score for gel clarity rating of the composition does not change by more than 1 unit on the clarity rating scale.

30. The method of claim 29 wherein the formulation, when dispensed, forms a gel with a clarity rating score of C=1.

* * * * *